United States Patent [19]

Fitzgerald

[11] 4,435,178
[45] Mar. 6, 1984

[54] DISPOSABLE ABSORBENT PRODUCT HAVING AN EMBOSSED PAD CONTAINING A GEL FORMING COMPOUND

[75] Inventor: Harry G. Fitzgerald, Green Bay, Wis.

[73] Assignee: Colgate-Palmolive Company, New York, N.Y.

[21] Appl. No.: 890,155

[22] Filed: Mar. 27, 1978

[51] Int. Cl.³ ............................................. A61F 13/16
[52] U.S. Cl. .................................... 604/365; 604/368; 604/379
[58] Field of Search ........... 128/284, 285, 287, 290 R, 128/296; 604/365, 368, 379

[56] References Cited

U.S. PATENT DOCUMENTS

| Re. 26,939 | 8/1970 | Hervey et al. | 128/284 |
|---|---|---|---|
| 1,863,333 | 6/1932 | Heitmeyer | 128/290 R |
| 2,418,907 | 4/1947 | Schreiber | 128/284 |
| 2,464,640 | 3/1949 | Fourness | 128/290 R |
| 2,508,214 | 5/1950 | Biederman | 128/285 |
| 2,548,341 | 7/1951 | Bricmont | 128/290 R |
| 2,896,626 | 7/1959 | Voigtman | 128/287 |
| 3,670,731 | 6/1972 | Harmon | 128/284 |
| 3,858,585 | 1/1975 | Chatterjee | 128/296 |
| 3,881,490 | 1/1975 | Whitehead et al. | 128/290 R |
| 3,900,378 | 8/1975 | Yen et al. | 128/284 |
| 3,929,135 | 12/1975 | Thompson | 128/287 |
| 3,934,588 | 1/1976 | Mesek et al. | 128/284 |
| 4,023,570 | 5/1977 | Chinai et al. | 128/290 R |
| 4,023,571 | 5/1977 | Comerford et al. | 128/296 |

Primary Examiner—C. Fred Rosenbaum
Attorney, Agent, or Firm—Herbert S. Sylvester; Murray M. Grill; Norman Blumenkopf

[57] ABSTRACT

A disposable product and a process for manufacturing the disposable product on a flexible conveyor. The disposable product has an absorbent core formed by sandwiching a corrugated tissue between two separate feeds of fluffed pulp. Upper and lower layers of wadding are provided, the lower wadding being first folded around the absorbent core longitudinally and then an upper wadding is laid on top. The upper and lower waddings are then roller crimped together and die cut and shaped and turned ninety degrees. Thereafter, a water impervious sheet of material, such as polyethylene, is provided with a glue line on its edges and is fed across the top wadding and wrapped about the top wadding, the core, and partially overlying the lower wadding. A sheet of non-woven material is then wrapped about the assembly and provided with a longitudinal strip or strips of pressure sensitive adhesive. A release paper is applied over the adhesive to protect it prior to use. The lower layer of fluffed pulp is embossed and printed to form coated recesses partially therethrough for accommodating and absorbing substantial discharges of material at a rate faster than otherwise possible so as to prevent leakage. These recesses are formed by the embossing and the coating is selected so that the recesses are stabilized. The material beneath the recesses are substantially compressed.

1 Claim, 7 Drawing Figures

U.S. Patent     Mar. 6, 1984     4,435,178
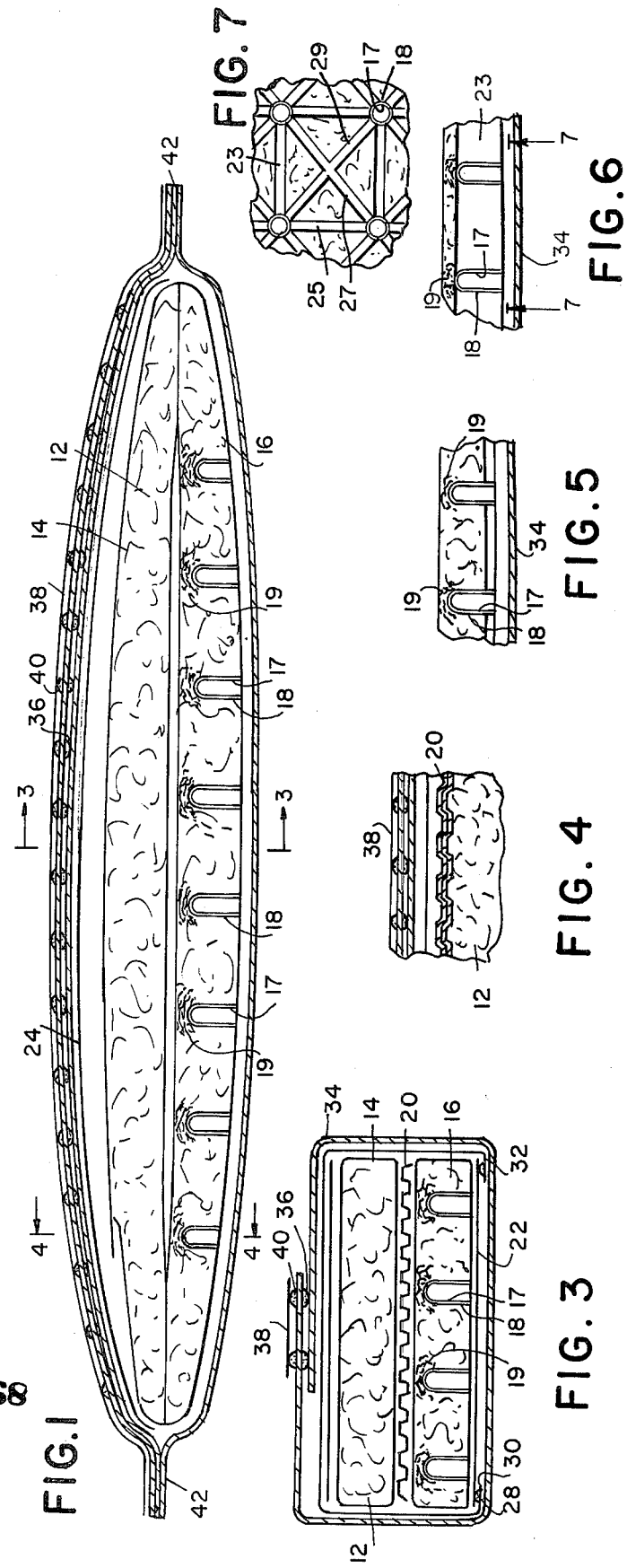

DISPOSABLE ABSORBENT PRODUCT HAVING AN EMBOSSED PAD CONTAINING A GEL FORMING COMPOUND

BACKGROUND OF THE INVENTION

1. Field of the Invention

This invention relates to a disposable product, such as a diaper or a sanitary napkin and a process of manufacturing the same.

2. The State of the Prior Art

Numerous patents exist on diapers and sanitary napkins and like disposable products provided with absorbent pads. There has been much activity in the field of developing absorbent cores. In the past, the cores have either been sufficiently absorbent to accept a substantial quantity of discharge or did not have the ability to accommodate fluid flooding and thereby prevent leaking because the core did not have provision for rapid reception of the quantities of fluid when discharged at a rapid rate. Alternatively, cores of prior diapers and sanitary napkins that were capable of preventing leakage when receiving gushes of fluid were unable to absorb sufficient total quantities of fluid over a practical period of time because the means for accommodating flooding reduced total fluid capacity.

Various means were used for absorption and transfer and distribution of fluid in a core such as the longitudinally corrugated paper in the middle of the core as shown in U.S. Pat. No. 2,896,627. Recesses and wells have been formed in the cores such as are shown in U.S. Pat. Nos. 3,593,717, 3,403,689, 3,046,986, and 3,749,627. In U.S. Pat. No. 3,666,611 there is disclosed a pulp layer having a central compressed portion. Embossing and folding has been used to enhance absorption quantities as disclosed in U.S. Pat. No. 2,952,260. Sanitary pads and diapers have been made on flexible conveyors as is disclosed in U.S. Pat. No. 3,291,131. Other pertinent patents relating to the method of manufacturing absorbent pads on flexible conveyors are U.S. Pat. Nos. 2,973,760, 3,268,954, 2,872,023, 3,225,898, 3,439,795, and 3,203,419.

SUMMARY OF THE INVENTION

The present invention overcomes the difficulties of the prior art by providing a process of manufacturing an absorbent pad for a diaper, sanitary napkin, or like disposable product, which simplifies the formation of the novel pad and which prevents loss of both total absorbability and accommodation of fluid flooding of the disposable product during the manufacture thereof thereby resulting in a disposable product capable of withstanding gushes of fluid, yet which has an extremely high total absorbability.

In carrying out the invention, two separate layers of fluffed pulp are fed onto a flexible conveyor sandwiching a two-ply corrugated tissue sheet therebetween. The pad is further formed by having one of the fluffed pulp layers embossed and printed to form spaced coated recesses therein, and underlying these recesses are substantially compressed portions. Upper and lower two-ply wadding is disposed under and above the fluffed pulp layers. A sheet of polyethylene or like fluid impervious material is wrapped about the upper fluffed pulp layer and the upper wadding extends so that its edges overlie and are adhesively secured to the edge portions of the lower wadding. The ends of the wadding are crimped and a sheet of non-woven material is wrapped about the assembly and secured by a pressure sensitive adhesive, which also serves as a means for securing the disposable product when in use. A release paper, e.g. silicone treated, is applied over the adhesive to protect it before use.

It is therefore an object of the invention to provide a disposable product having spaced coated recesses therein which may communicate with each other. The recesses are formed by embossing so that the material therebelow is highly compressed. Embossing and thereby forming recesses having compressed portions therebelow is desirable because the gushes of waste fluid are easily received and accommodated by the recesses, but the compressed portions prevent fluid from gushing through the pad at the compressed locations therefore enhancing waste fluid distribution.

BRIEF DESCRIPTION OF THE DRAWING

FIG. 1 is a longitudinal sectional view of an embodiment of the invention in the form of a sanitary napkin;

FIG. 2 is a plan view of the sanitary napkin with parts thereof being broken away;

FIG. 3 is a vertical sectional view taken along the plane of line 3—3 in FIG. 2;

FIG. 4 is a partial sectional view taken along the plane of line 4—4 in FIG. 2;

FIG. 5 is a partial sectional view showing a lower layer provided with shallow grooves intercommunicating the recesses;

FIG. 6 is a view similar to FIG. 5, but showing deep grooves; and,

FIG. 7 is a partial plan view of the intercommunicating grooves.

DETAILED DESCRIPTION OF THE INVENTION

With continuing reference to the accompanying drawing, wherein like reference numerals designate similar parts throughout the various views, reference numeral 10 is used to generally designate a disposable product in the form of a sanitary napkin which includes an absorbent core 12. This invention is equally applicable to a disposable diaper or like product. The absorbent core 12 includes an upper layer 14 of fluffed pulp and a lower layer 16 of fluffed pulp having recesses 18 provided with coatings 17 therein which extend almost, but not all the way, through the fluffed pulp layer 16. The recesses 18 are arranged to face the wearer. The recesses 18 are about four fifths the thickness of the lower layer 16. The recesses 18 are formed by hot or cold embossing and simultaneous printing which serves to compress the material 19 underlying the recesses while providing a coating of a water soluable binding material selected from starches, dextrous, carboxy methyl cellulose, polyvinyl alcohol, hydrolized polyvinyl acetate. It is within the special contemplation of the invention to use the so called super absorbing polymers derived from polyacrylo nitrile, poly acrile amide and starches grafted therewith so as to increase by far absorption. The coatings on the recesses and grooves serve to stabilize the recesses and maintain the shape of the absorbent pad. The embossing simultaneously prints with a coating of the water soluable binding material. Shallow coated grooves 21 may interconnect the recesses 18 shown in FIG. 5. These grooves may form spaced lines of recesses. The grooves 19 are not as deep as the recesses 18. Alternatively linear coated grooves 23 as well as transverse coated grooves 25 and diagonal coated grooves 27 and 29 may interconnect each recess with all adjacent recesses. These grooves may be as deep as the recesses and provide for optimum fluid distribution.

A two-ply corrugated sheet of tissue 20 is sandwiched between the fluffed pulp layers 14 and 16. Below the layer 16 is a two-ply wadding 22, while an upper two-ply wadding 24 overlies the upper surface of the fluffed pulp layer 14. A sheet of water impervious material 26, such as polyethylene, overlies the wadding 24 and extends about the core 12 and is secured to the edges of the lower wadding 22 by adhesive or glue 28 provided on flange portions 30 and 32. The flange portions do not extend under the recesses 18. A sheet 34 of non-woven material which overlies the lower wadding 22 is wrapped to overlie the upper wadding 24 and the water impervious sheet 26 and may have its edges secured by pressure sensitive adhesive 36. A strip 38 of silicone-release paper 38 is provided with pressure sensitive adhesive 40 and is secured to overlie the non-woven sheet 34. The ends of the wadding layers 24 and 22 and the ends of the non-woven sheet 34 are roller crimped together as at 42. The coated recesses and grooves 21 or 23 provide means for accommodating gushes of fluid while the corrugated tissue 20, which is corrugated lengthwise, provides for fluid distribution from the absorbent pulp layer 16 to the absorbent fluffed pulp layer 14. The compressed areas 19 under the recesses and grooves prevent flooding of the corrugated tissue 20. The non-woven sheet 34 provides for a dry contacting surface, while the water impervious sheet 26 assures against leaking. The coating for the grooves and recesses serve to stabilize the recesses and grooves and maintain the shape of the pad. When the super absorbing material is used, absorption is enhanced.

The sanitary napkin is manufactured on an endless belt conveyor using two separate sheets of fluffed pulp, which are laid one over the other sandwiching the corrugated two-ply tissue 20 therebetween. The bottom layer of fluffed pulp is formed with the coated recesses 18 and grooves 19 therein. The absorbent core is laid on the lower wadding 22, which is two-ply, and which is folded around the absorbent core longitudinally with the top wadding 24 being laid on top and the top and bottom waddings are roller crimped together. Then, the strip assembly is die shaped and cut and then turned ninety degrees so that a sheet of polyethylene 26 may be fed across the top and folded around and bonded by its glue lines to the lower wadding 22. Thereafter, the napkin is wrapped with the non-woven sheet 34 and its edges secured by adhesive, which also serves to hold a silicone-release paper thereon for sealing purposes when the pad is not in use.

Many modifications and variations of the sanitary napkin and the process of manufacturing may be made within the light of this disclosure and it is to be understood that the invention may therefore be practiced within the scope of the appended claims.

What is claimed is:

1. A disposable product comprising an absorbent core having a corrugated tissue sandwiched between two layers of fluffed pulp, upper and lower layers of wadding above and below said absorbent core, a fluid impervious sheet wrapped about said upper wadding layer and said absorbent core and having edges bonded to said lower wadding layer, and a non-woven sheet material wrapped about said wadding, core, and fluid impervious sheet, the lower layer of said layers of fluffed pulp facing the wearer and being provided with embossed recesses therein, said recesses extending about four-fifths the thickness of said lower layer of fluffed pulp and the material of said lower layer of fluffed pulp above said re-esses being highly compressed, said recesses being coated with a stabilizing binding material selected from polymers derived from poly acrylo nitrile, poly acrylamide and starches grafted therewith, said lower layer of fluffed pulp having grooves in the lower layer interconnecting said recesses.

* * * * *